United States Patent [19]
Bass et al.

[11] Patent Number: 5,977,142
[45] Date of Patent: Nov. 2, 1999

[54] OXA-AND THIA-DIAZOLE MUSCARINIC RECEPTOR ANTAGONISTS

[75] Inventors: Robert John Bass; Alexander Roderick MacKenzie; Anthony Wood, all of Sandwich, United Kingdom

[73] Assignee: Pfizer Inc., New York, N.Y.

[21] Appl. No.: 09/117,556

[22] PCT Filed: Feb. 4, 1997

[86] PCT No.: PCT/EP97/00525

§ 371 Date: Jul. 31, 1998

§ 102(e) Date: Jul. 31, 1998

[87] PCT Pub. No.: WO97/30994

PCT Pub. Date: Aug. 28, 1997

[30]    Foreign Application Priority Data

Feb. 22, 1996 [GB] United Kingdom .................. 9603755

[51] Int. Cl.[6] ...................... A61K 31/445; C07D 413/04; C07D 417/04
[52] U.S. Cl. .......................... 514/326; 546/208; 546/209; 546/210
[58] Field of Search ............................. 514/326; 546/208, 546/209, 210

[56]    References Cited

U.S. PATENT DOCUMENTS

| 5,686,463 | 11/1997 | Baker et al. | 514/299 |
| 5,712,297 | 1/1998 | Sauerberg et al. | 514/342 |
| 5,854,261 | 12/1998 | Bosmans | 514/320 |

FOREIGN PATENT DOCUMENTS 323864  7/1989  European Pat. Off. .

9313083  7/1993  WIPO .

OTHER PUBLICATIONS

Saunders et al., J. Med. Chem., 33, 1128–38 (1990).

MacLeod et al. J. Med Chem., 33,2052–59 (1990).

Bidaut–Russell et al. "Muscarinic pharmacology of the inhibition of . . . " Ca 108:31798, 1987.

*Primary Examiner*—Ceila Chang
*Attorney, Agent, or Firm*—Peter C. Richardson; Gregg C. Benson; Gregory P. Raymer

[57]    ABSTRACT

A compound of formula (I)

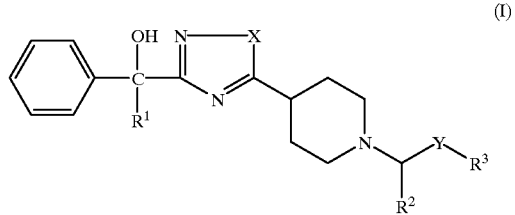

wherein $R^1$ is $C_{1-6}$ alkyl, halo-($C_{1-6}$ alkyl), $C_{3-7}$ cycloalkyl, $C_{2-6}$ alkylnyl, hydroxy-($C_{2-6}$ alkylnyl), ($C_{1-4}$ alkoxy)-($C_{2-6}$ alkylnyl), aryl, aryl-($C_{1-4}$ alkyl), heteroaryl or heteroaryl-($C_{1-4}$ alkyl); $R^2$ is H or $C_{1-4}$ alkyl; $R^3$ is aryl, heteroaryl, 2,3-dihydrobenzofuranyl or $C_{4-7}$ cycloalkyl; X is O or S; Y is bond, —$CH_2$—, —$(CH_2)_2$— or —$CH_2O$—, a pharmaceutically acceptable salt thereof, which are useful muscarinic receptor antagonists in treaatment of e.g. irritable bowel syndrome, urinary incontinence, etc.

23 Claims, No Drawings

OXA-AND THIA-DIAZOLE MUSCARINIC RECEPTOR ANTAGONISTS

This application is a 371 of PCT/EP97/00525 filed Feb. 4, 1997.

This invention relates to substituted oxadiazole and thiadiazole derivatives. The compounds of the invention are muscarinic receptor antagonists which are selective for smooth muscle muscarinic sites over cardiac muscarinic sites and which do not have any significant antihistaminic activity. Thus the compounds are useful in the treatment of diseases associated with altered motility and/or tone of smooth muscle which can, for example, be found in the gut, trachea and bladder. Such diseases include irritable bowel syndrome, diverticular disease, urinary incontinence, oesophageal achalasia and chronic obstructive airways disease.

The compounds are also useful as cognition enhancers, and are thus useful in treating diseases involving memory impairment such as Alzheimer's disease and age-related memory disorder.

According to the invention there are provided compounds of the formula:

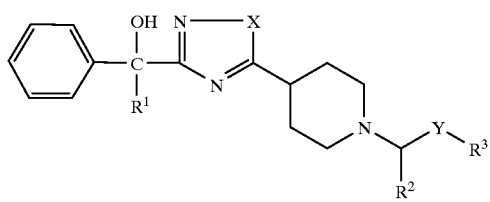

wherein $R^1$ is $C_1$–$C_6$ alkyl, halo-($C_1$–$C_6$ alkyl), $C_3$–$C_7$ cycloalkyl, $C_2$–$C_6$ alkynyl, hydroxy-($C_2$–$C_6$ alkynyl), ($C_1$–$C_4$ alkoxy)-($C_2$–$C_6$ alkynyl), aryl, aryl-($C_1$–$C_4$ alkyl), heteroaryl or heteroaryl-($C_1$–$C_4$ alkyl);

$R^2$ is H or $C_1$–$C_4$ alkyl;

$R^3$ is aryl, heteroaryl, 2,3-dihydrobenzofuranyl or $C_4$–$C_7$ cycloalkyl;

X is O or S;

and Y is a direct link, —$CH_2$—, —$(CH_2)_2$— or —$CH_2O$—;

and their pharmaceutically acceptable salts.

By halo is meant chloro, bromo, fluoro or iodo.

Preferred aryl groups are phenyl and naphthyl both optionally substituted by up to 3 substituents each independently selected from $C_1$–$C_4$ alkyl, $C_1$–$C_4$ alkoxy, hydroxy, halo and trifluoromethyl.

More preferably, the aryl groups are selected from phenyl optionally substituted by 1 or 2 substituents each independently selected from $C_1$–$C_4$ alkyl, $C_1$–$C_4$ alkoxy, hydroxy, halo and trifluoromethyl; and naphthyl.

Most preferably, the aryl group is phenyl, fluorophenyl, dichlorophenyl, hydroxyphenyl, methoxyphenyl or naphthyl.

Preferred heteroaryl groups are thienyl, pyridyl, thiazolyl, benzothiazolyl, thiadiazolyl, pyrazolyl and pyrimidinyl, all optionally substituted by 1 or 2 substituents each independently selected from $C_1$–$C_4$ alkyl, $C_1$–$C_4$ alkoxy, hydroxy and halo.

More preferred heteroaryl groups are thienyl, pyridyl, thiazolyl and benzothiazolyl.

Preferred alkyl groups are methyl and ethyl. Preferred alkoxy groups are methoxy and ethoxy. Preferred halo groups are chloro, bromo and fluoro. Preferred cycloalkyl groups are cyclobutyl, cyclopentyl and cyclohexyl, particularly cyclobutyl. The preferred alkynyl group is ethynyl. Preferred hydroxy-($C_2$–$C_6$ alkynyl) groups are HO—$CH_2C$≡C— and HO—$(CH_2)_4$—C≡C—. The preferred haloalkyl groups are trifluoromethyl and pentafluoroethyl.

$R^1$ is preferably $C_1$–$C_6$ alkyl; pentafluoroethyl; $C_4$–$C_6$ cycloalkyl; ethynyl; —C—C—$CH_2OH$; —C≡C—$(CH_2)_4OH$; a phenyl group optionally substituted by 1 or 2 substituents each independently selected from halo, $C_1$–$C_4$ alkyl, $C_1$–$C_4$ alkoxy and hydroxy; naphthyl; or a heterocyclic group selected from thienyl, pyridyl, thiazolyl and benzothiazolyl, all optionally substituted by halo, $C_1$–$C_4$ alkyl, $C_1$–$C_4$ alkoxy or hydroxy.

$R^2$ is preferably H or $CH_3$.

$R^3$ is preferably either phenyl optionally substituted by 1 or 2 substituents each independently selected from halo, $C_1$–$C_4$ alkyl, $C_1$–$C_4$ alkoxy and hydroxy; 2,3-dihydrobenzofuranyl; $C_4$–$C_7$ cycloalkyl or thienyl.

X is preferably O.

Y is preferably a direct link, —$CH_2$— or —$CH_2O$—.

The pharmaceutically acceptable salts of the compound of formula (I) include acid addition salts such as the hydrochloride, hydrobromide, hydrofluoride, sulphate or bisulphate, phosphate or hydrogen phosphate, acetate, besylate, citrate, fumarate, gluconate, lactate, maleate, mesylate, succinate and tartrate salts. For a more comprehensive list of pharmaceutically acceptable salts see, for example, the Journal of Pharmaceutical Sciences, Vol. 66, No. 1, January 1977, pages 1–19. These salts can be prepared conventionally, e.g. by mixing a solution of the free base and the acid in a suitable solvent, e.g. ethanol, and recovering the acid addition salt either as a precipitate, or by evaporation of the solution.

The compounds (I) may contain one or more optically active centres and the invention includes both the separated and unseparated forms. The separated forms can be obtained by conventional means, e.g. by using high performance liquid chromatography employing a chiral stationary phase, or by chemical resolution via the formation of suitable salts or derivatives.

One method to the compounds (I) is via the ketones (II):

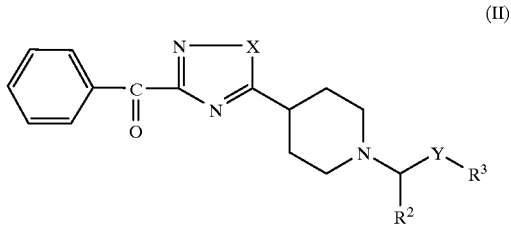

where X, Y, $R^2$ and $R^3$ are as defined for formula (I), by reaction with a Grignard, organolithium or organocerium reagent of the formula:

$R^1MgHal$, $R^1Li$ or $R^1CeCl_2$ where Hal is Cl or Br, in a suitable organic solvent.

When an organolithium or organocerium reagent is used, the reaction is typically carried out at low temperature, i.e. at 0° C. or below, and preferably at about −78° C.

A preferred organic solvent is tetrahydrofuran.

The preferred Grignard reagents are the magnesium bromides.

The Grignard reagents can be generated in situ, e.g. by adding a halide of the formula $R^1Hal$ dropwise to a suspension of magnesium turnings in an organic solvent such as diethyl ether at a rate sufficient to maintain reflux. After stirring for, say, about 30 minutes at room temperature, the resulting solution containing the Grignard reagent is added dropwise to a solution of the ketone (II) in a suitable organic solvent, typically at a temperature of 0° to −20° C.

The product can be isolated from the reaction mixture conventionally.

The novel intermediates (II) also form a part of the invention.

The intermediates (II) in which X is O are preparable by conventional techniques, e.g. as follows:

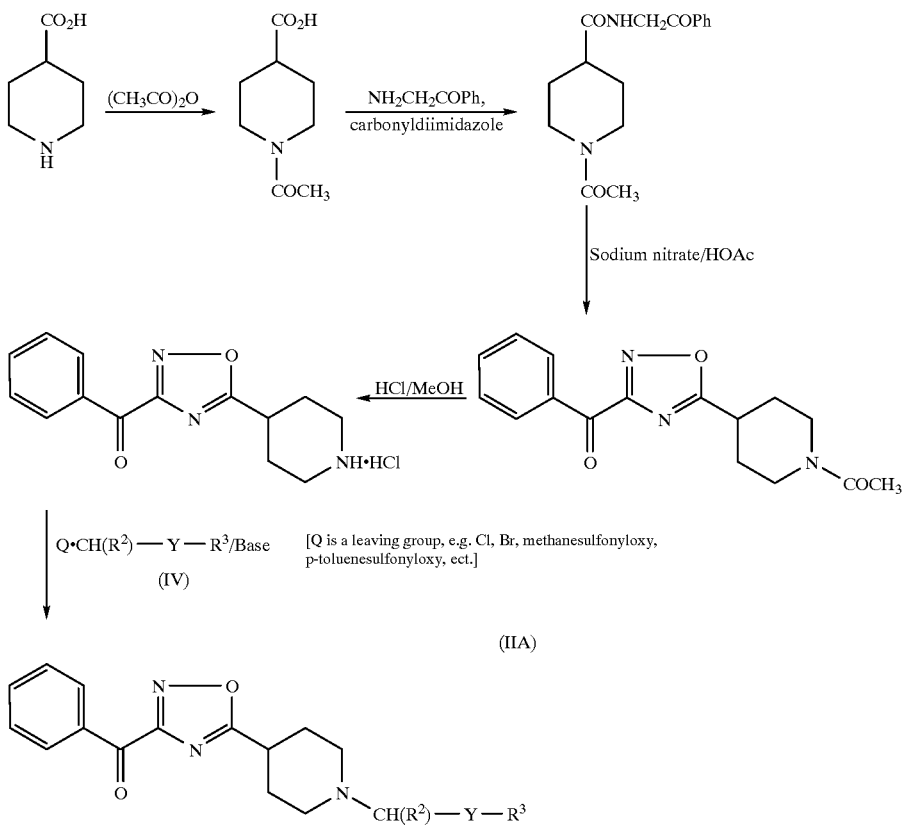

An alternative route to the intermediates (IIA) is as follows:

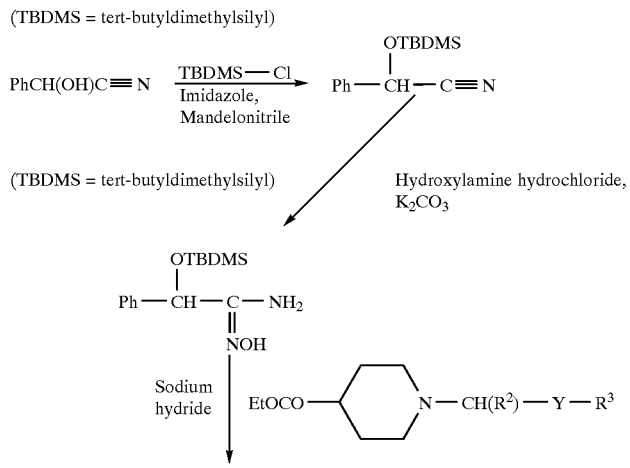

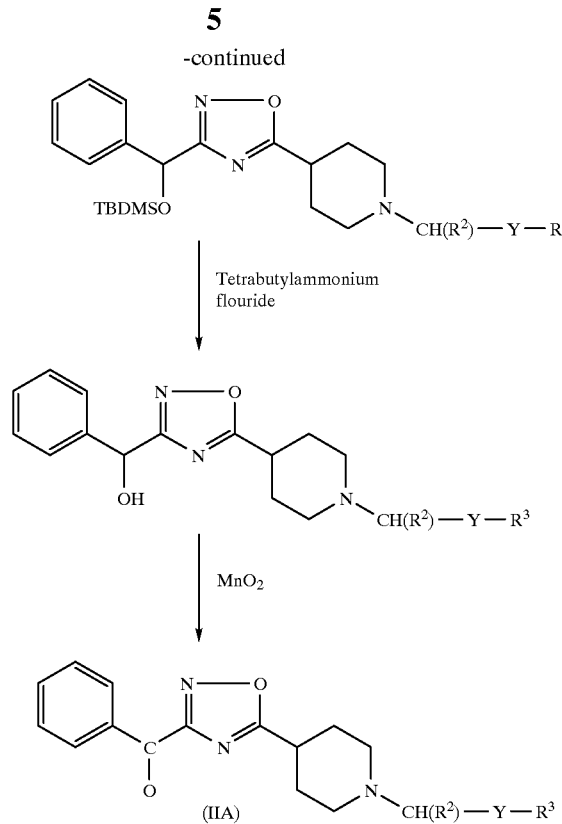
Routes to the thiadiazole intermediates are as follows:
(a)
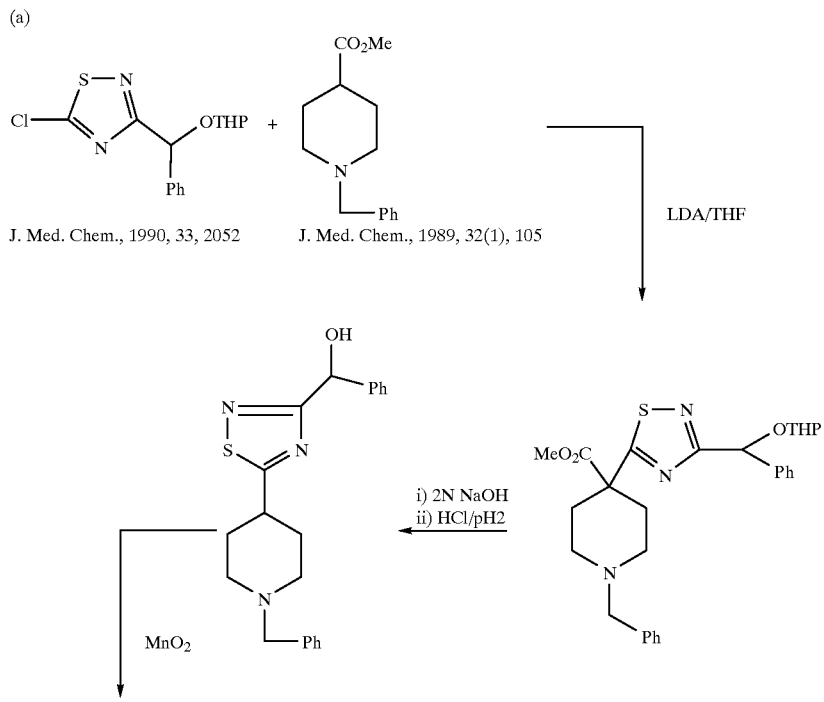

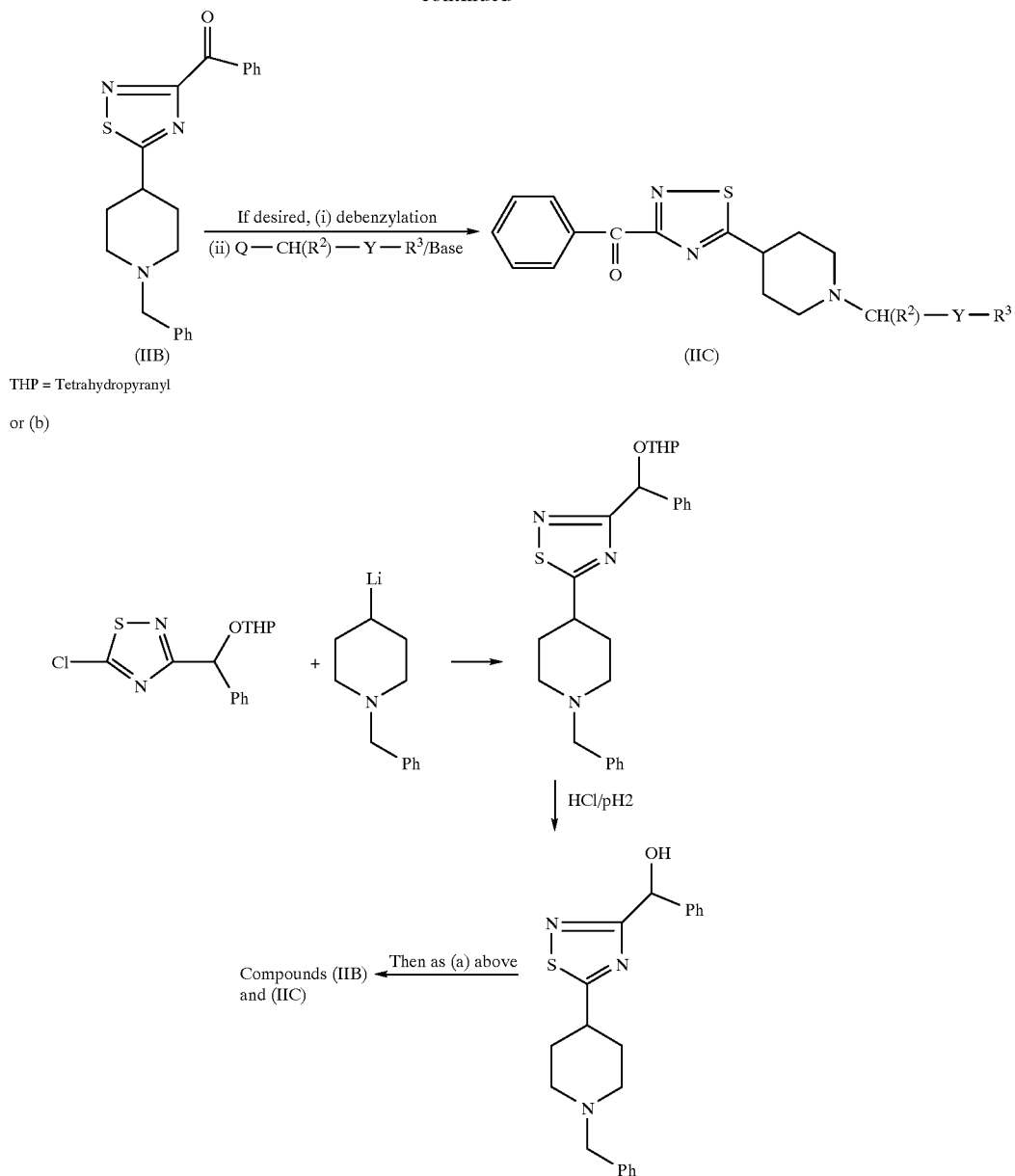

THP = Tetrahydropyranyl

Another method to the compounds (I) is from a hydroxy-containing compound (III) or base salt thereof:

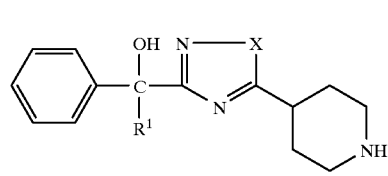

(III)

wherein $R^1$ and X are as defined for formula (I), either (a) by reaction with a compound of the formula (IV):

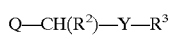 (IV)

wherein Q is a leaving group such as tosyloxy, mesyloxy, trifluoromethanesulfonyloxy, Cl or Br and $R^2$, $R^3$ and Y are as defined for formula (I); or (b), by reaction with an aldehyde or ketone of the formula

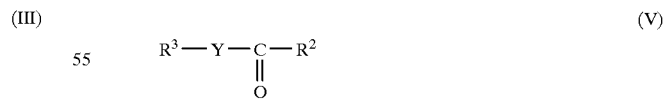

(V)

wherein $R^2$, $R^3$ and Y are as defined for formula (I), in the presence of a reducing agent, e.g. sodium triacetoxyborohydride or sodium cyanoborohydride, in a suitable organic solvent, e.g. tetrahydrofuran, and typically at room temperature.

When the free base of compound (III) is used in (a), the reaction is typically carried out in the presence of an acid acceptor such as sodium bicarbonate or ethyidiisopropylamine.

The compounds of the formula (III) can be prepared by removal of the benzyl group from the compounds of the formula (I) in which the group "—CH(R²)—Y—R³" is benzyl, typically by reaction with a suitable chloroformate, e.g. α-chloroethylchloroformate, in a suitable organic solvent, e.g. dichloromethane or toluene, and preferably under reflux.

The selectivity of the compounds (I) as muscarinic receptor antagonists can be measured as follows.

Male guinea pigs are sacrificed and the ileum, trachea, bladder and right atrium are removed and suspended in physiological salt solution under a resting tension of 1 g at 32° C. aerated with 95% $O_2$ and 5% $CO_2$. Contractions of the ileum, bladder and trachea are recorded using an isotonic (ileum) or isometric transducer (bladder and trachea). The frequency of contraction of the spontaneously beating right atrium is derived from isometrically recorded contractions.

Dose-response curves to either acetylcholine (ileum) or carbachol (trachea, bladder and right atrium) are determined using a 1–5 minute contact time for each dose of agonist until the maximum response is achieved. The organ bath is drained and refilled with physiological salt solution containing the lowest dose of the test compound. The test compound is allowed to equilibrate with the tissue for 20 minutes and the agonist dose-response curve is repeated until the maximum response is obtained. The organ bath is drained and refilled with physiological salt solution containing the second concentration of test compound and the above procedure is repealed. Typically four concentrations of the test compound are evaluated on each tissue.

The concentration of the test compound which Causes a doubling of the agonist concentration to produce the original response is determined ($pA_2$ value—Arunlakshana and Schild (959), Brit. J. Pharmacol., 14, 48–58). Using the above analytical techniques, tissue selectivity for muscarinic receptor antagonists is determined.

Activity against agonist induced broncho-constriction or gut or bladder contractility in comparison with chances in heart rate is determined in the anaesthetised dog. Oral activity is assessed in the conscious dog determining compound effects on, for example, heart rate, pupil diameter and cut motility.

Compound affinity for other cholinergic sites is assessed in the mouse after either intravenous or intraperitoneal administration. Thus, the dose which causes a doubling of pupil size is determined as well as the dose which inhibits the salivation and tremor responses to intravenous oxotremorine by 50%.

For administration to man in the curative or prophylactic treatment of diseases associated with the altered motility and/or tone of smooth muscle, such as irritable bowel syndrome, diverticular disease, urinary incontinence, oesophageal achalasia and chronic obstructive airways disease, oral dosages of the compounds will generally be in the range of from 3.5 to 350 mg daily for an average adult patient (70 kg). Thus for a typical adult patient, individual tablets or capsules will typically contain from 1 to 250 mg of active compound, in a suitable pharmaceutically acceptable vehicle or carrier for administration singly or in multiple doses, once or several times a day. Dosages for intravenous administration will typically be within the range 0.35% to 35 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compound of the formula (I) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

In a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I) or a pharmaceutically acceptable salt thereof, for use as a medicament, particularly for use in the treatment of urinary incontinence or irritable bowel syndrome.

The invention further includes the use of a compound of the formula (I), or of a pharmaceutically acceptable salt thereof, for the manufacture of a medicament for the treatment of diseases associated with the altered motility and/or tone of smooth muscle, such as irritable bowel syndrome, diverticular disease, urinary incontinence, oesophageal achalasia and chronic obstructive airways disease.

The invention yet further includes any novel intermediates described herein.

The synthesis of the compounds of the formula (I), and of certain intermediates for use therein, are illustrated by the following Examples and Preparations, respectively.

The purity of compounds was routinely monitored by thin layer chromatography using Merck Kieselgel 60 $F_{254}$ plates. $^1$H Nuclear magnetic resonance (nmr) spectra were recorded using Bruker AC-300 and Varian Unity 300 spectrometers and were in all cases consistent with the proposed structures. Chemical shifts are given in parts per million (δ) downfield from tetramethylsilane using standard conventional abbreviations for the designation of major peaks, e.g singlet (s), doublet (d), doublet of doublets (dd), triplet (t), quartet (q), multiplet (m), and broad (b). LRMS means low resolution mass spectrum. Room temperature is 20–25° C.

PREPARATION 1

1-Acetylpiperidine-4-carboxylic acid

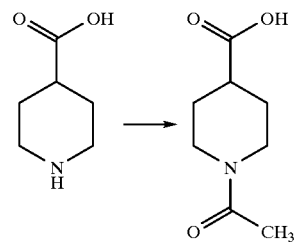

Piperidine-4-carboxylic acid (208 g, 1.63 moles) was dissolved in acetic anhydride and the resulting solution heated at reflux under a nitrogen atmosphere for 48 hours. The flask contents were allowed to cool then concentrated under reduced pressure to give a pale yellow oil which solidified on standing. Recrystallisation from propan-2-ol then afforded the title compound as an off white solid (160 g, 0.94 moles, 58%), mp 164–166° C. (IPA-ethylacetate), $\delta_H$ (300 MHz;CDCl$_3$) 1.7 (2H, m), 2.0 (2H, m), 2.2 (3H, s), 2.6 (1H, m), 2.85 (1H, m), 3.2 (1H, m), 3.8 (1H, m), and 4.4 (1H, m).

PREPARATION 2

1-Acetylpiperidine-4-(2-oxo-2-phenylethyl) carboxamide

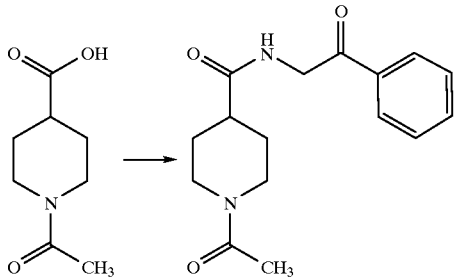

Carbonyldiimidazole (CDI) (212.0 g, 1.31 moles) was added portionwise to a stirred suspension of 1-acetylpiperidine-4-carboxylic acid (200.0 g, 1.17 moles) in dry dichloromethane under nitrogen at room temperature [care CO$_2$ evolution]. The resulting solution was then stirred at room temperature under nitrogen for 2 hours. α-Aminoacetophenone hydrochloride (210 g, 1.22 moles) was added followed by triethylamine (170 cm$^3$, 1.22 moles) causing a slight exotherm. The resulting mixture was stirred at ambient temperature under nitrogen overnight. The flask contents were then washed with aqueous hydrochloric acid (2l, 2M) and deionised water (2×1 l), dried over anhydrous sodium sulphate and concentrated under reduced pressure to give the title compound as an orange solid (300 g, 1.04 moles, 79%), Rf 0.15 (95:5 CH$_2$Cl$_2$:MeOH), mp 161–162° C., $\delta_H$ (300 MHz;CDCl$_3$) 1.7 (2H, m), 1.9 (2H, m), 2.1 (3H, s), 2.5 (1H, m), 2.7 (1H, t), 3.1 (1H, t), 3.9 (1H, d), 4.6 (1H, d), 4.8 (2H, d), 6.6 (1H, s), 7.5 (2H, m), 7.6 (1H, m), and 7.9 (2H, d).

PREPARATION 3

3-Benzoyl-5-{4-(1-acetylpiperidinyl)}-1,2,4-oxadiazole

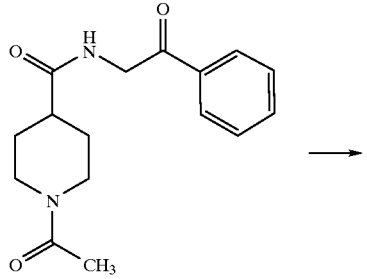

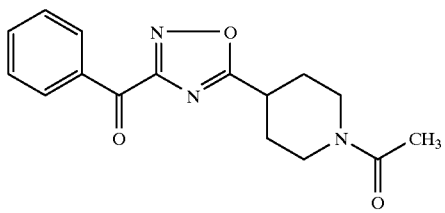

1-Acetylpiperidine-4-(2-oxo-2-phenylethyl)carboxamide (294 g, 1.02 moles) was dissolved in glacial acetic acid (1.5 l) with gentle warming. A solution of sodium nitrite (100 g) in deionised water (120 cm$^3$) was then added dropwise over a period of 2 hours with slight cooling from an ice-water bath. The resulting reaction mixture was stirred at ambient temperature for 144 hours adding further sodium nitrite (100 g) in deionised water (120 cm$^3$) every 48 hours. The flask contents were then purged with nitrogen and concentrated under reduced pressure to give a solid residue which was dissolved in dichloromethane (2.5 l) and washed successively with deionised water (500 cm$^3$), aqueous sodium hydroxide (200 cm$^3$, 10% w/v), and deionised water (500 cm$^3$). The resulting organic fraction was dried over anhydrous sodium sulphate and concentrated under reduced pressure to give the title compound as a pale yellow solid, (231 g, 0.77 moles, 77%), Rf 0.26 (95:5 CH$_2$Cl$_2$:MeOH), mp 97–100° C. $\delta_H$ (300 MHz;CDCl$_3$) 1.9 (2H, m), 2.1 (3H, s), 2.2 (2H, m), 2.9 (1H, t), 3.3 (2H, m), 3.9 (1H, d), 4.5 (1H, d), 7.5 (2H, t), 7.6 (1H, t), and 8.2 (2H, d); m/z (LRMS) 322 (MNa$^+$), 317 (MNH$_4^+$), and 300 (MH$^+$).

PREPARATION 4

3-Benzoyl-5-(4-piperidinyl)-1,2,4-oxadiazole hydrochloride

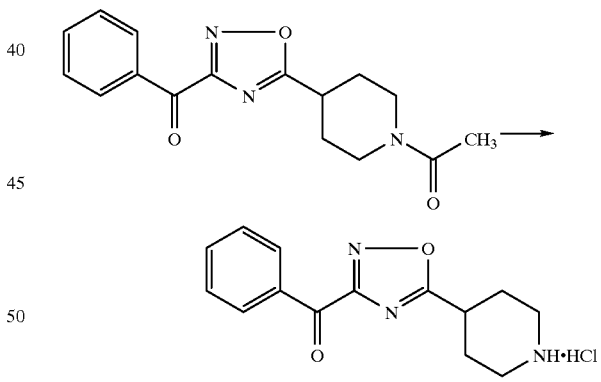

3-Benzoyl-5-{4-(1-acetylpiperidinyl)}-1,2,4-oxadiazole (230 g, 0.77 moles) was dissolved in HCl saturated methanol (2.5 l) and heated at reflux for 24 hours. The flask contents were then allowed to cool and concentrated hydrochloric acid (10 cm$^3$) was added. The reaction mixture was then heated at reflux for a further 20 hours after which tlc showed no starting material remaining. The flask contents were then cooled in an ice-acetone bath producing a white solid which was filtered and washed with ethyl acetate to afford the title compound (175 g, 0.58 moles, 75%), mp 224–227° C., $\delta_H$ (300 MHz;CDCl$_3$) 2.1 (2H, m), 2.3 (2H, m), 3.1 (2H, m), 3.3 (2H, m), 3.6 (1H, m), 7.6 (2H, m), 7.8 (1H, m), and 9.1 (1H, s); m/z (LRMS) 258 (MH$^+$).

PREPARATION 5

3-Benzoyl-5-{4-(1-benzylpiperidinyl)}-1,2,4-oxadiazole

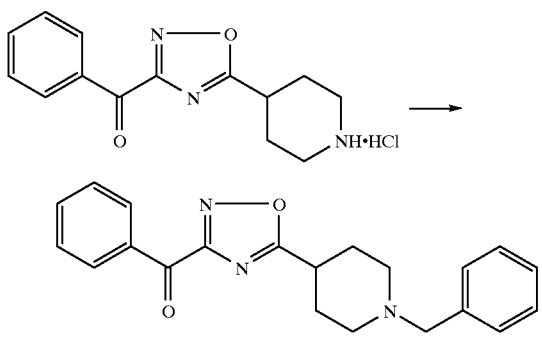

Benzyl bromide (67 cm³, 0.56 moles) was added to a mixture of 3-benzoyl-5-(4-piperidinyl)-1,2,4-oxadiazole hydrochloride (165 g, 0.56 moles) and solid potassium carbonate (194 g, 1.40 moles) in butan-2-one (1.6 l). The flask contents were then stirred at ambient temperature under nitrogen for 48 hours. Deionised water (1.3 l) was then added and the mixture stirred vigorously for 1 hour. The organic layer was collected and the remaining aqueous fraction extracted with ethyl acetate (500 cm³).

The combined organic fractions were then dried over anhydrous sodium sulphate and concentrated to give a pale yellow oil. Flash chromatography (1 kg "Kieselgel 60"™ silica) eluting with 8% methanol in dichloromethane gave a colourless oil which was azeotroped with toluene to afford the title compound as a white solid (177 g, 0.51 moles, 91%), Rf 0.6 (95:5 $CH_2Cl_2$:MeOH), mp 67–69° C., $\delta_H$ (300 MHz;$CDCl_3$) 2.1 (6H, m), 2.9 (2H, d), 3.1 (1H, m), 3.6 (2H, s), 7.3 (5H, m), 7.5 (2H, t), 7.7 (1H, t), and 8.3 (2H, d); m/z (LRMS) 348 ($MH^+$).

PREPARATION 6

2-tert-Butyldimethylsiloxyphenylacetonitrile

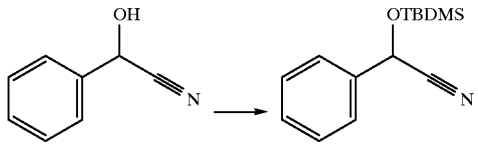

Mandelonitrile (50 g, 0.38 moles) and imidazole (64 g, 0.94 moles) were dissolved in DMF (100 cm³) and the resulting solution cooled in an ice-water bath. tert-Butyldimethylsilyl chloride (68 g, 0.45 moles) was then added portionwise over a period of 20 minutes. The flask contents were then warmed to 35° C. and stirred at that temperature for 18 hours. The reaction mixture was then cooled and partitioned between ethyl acetate (3×100 cm³) and deionised water (100 cm³). The combined organic fractions were then washed with brine (100 cm³), dried over anhydrous magnesium sulphate and concentrated under reduced pressure to give the crude product as a yellow oil. Flash chromatography (600 g kieselgel 60 silica) eluting with 20% dichloromethane in pentane gave the title compound as an oil (77 g, 0.31 moles, 82%), $\delta_H$ (300 MHz;$CDCl_3$) 0.1 (3H, s), 0.2 (3H, s), 1.0 (9H, s), 5.5 (1H, s), and 7.4 (5H, m).

PREPARATION 7

α-tert-Butyldimethylsiloxybenzylamidoxime

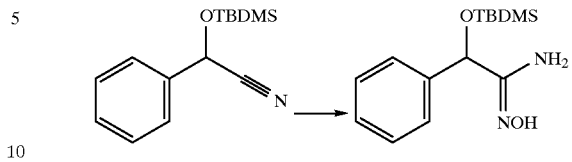

Solid potassium carbonate (54 g, 0.39 moles) was added to a mixture of 2-tert-butyldimethylsiloxyphenylacetonitrile (45 g, 018 moles) and hydroxylamine hydrochloride (25 g, 0.36 moles) in ethanol (450 cm³) and the resulting mixture heated at reflux under nitrogen for 2 hours. The flask contents were then cooled and concentrated under reduced pressure. The resulting residue was partitioned between dichloromethane (3×150 cm³) and deionised water (100 cm³). The combined organic fractions were then washed with brine (100 cm³), dried over anhydrous magnesium sulphate and concentrated under reduced pressure to give the title compound as a yellow solid(53.2 g, 0.18 motes, 100%). $\delta_H$ (300 MHz;$CDCl_3$) 0.1 (3H, s), 0.2 (3H, s), 1.0 (9H, s), 4.8 (2H, bs), 5.3 (1H,bs), 7.3 (3H, m), and 7.5 (2H, m).

PREPARATION 8

3-(α-tert-Butyldimethylsiloxybenzyl)-5-{4-(1-benzylpiperidinyl)}1,2,4-oxadiazole

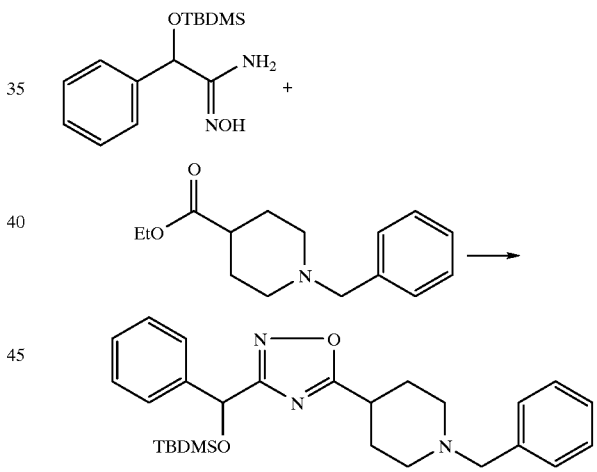

α-tert-Butyldimethylsiloxybenzylamidoxime (53.2 g, 0.18 moles) was dissolved in THF (400 cm³) and powdered 4 Å sieves (10 g) were added. The resulting mixture was heated at reflux under nitrogen for 15 minutes then cooled in an ice-bath. Sodium hydride (8.0 g, 60% dispersion, 0.2 moles) was added portionwise and the flask contents were allowed to warm to room temperature slowly so as to control effervescence. When hydrogen evolution had ceased, a solution of ethyl N-benzylpiperidine-4-carboxylate (45 g, 0.18 moles) in THF (125 cm³) was added dropwise. The flask contents were stirred at ambient temperature for 30 minutes then heated at reflux under nitrogen for 1.5 hours. After cooling the reaction mixture was partitioned between ethyl acetate (2×200 cm³) and deionised water (200 cm³). The combined organic fractions were then washed with brine (100 cm³), dried over anhydrous magnesium sulphate and concentrated under reduced pressure to give the title compound as a tan coloured oil (62 g, 0.13 moles, 72%), δ$_H$ (300 MHz;CDCl$_3$) 0.1 (3H, s), 0.2 (3H, s), 1.0 (9H, s), 2.0 (6H, m), 2.9 (3H, m), 3.5 (2H, s), 6.0 (1H, s), 7.3 (8H, m), and 7.5 (2H, m).

PREPARATION 9

3-(α-hydroxybenzyl)-5-{4-(1-benzylpiperidinyl)}-1,2,4-oxadiazole

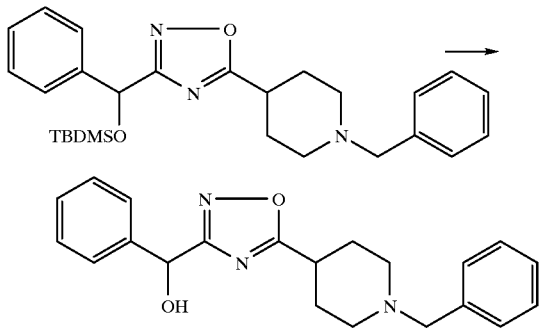

Tetrabutyl ammonium fluoride (237 cm$^3$, 1M in THF) was added dropwise to a stirred solution of 3-(α-tert-butyldimethylsiloxybenzyl)-5-{4-(1-benzylpiperidinyl)}-1,2,4-oxadiazole (62 g, 0.13 moles) in THF (200 cm$^3$) at 0° C. The resulting mixture was then allowed to warm to room temperature and stirred for a further 30 minutes. The flask contents were then partitioned between ethyl acetate (3×200 cm$^3$) and deionised water (200 cm$^3$) and the combined organic fractions washed with brine (100 cm$^3$), dried over anhydrous magnesium sulphate and concentrated under reduced pressure to give the title compound as a yellow solid (45.0 g) (Found C, 70.5;H, 6.5; N, 11.8. C$_{21}$H$_{23}$N$_3$O$_2$.½H$_2$O requires C, 70.4; H, 6.8; N, 11.7%); δ$_H$ (300 MHz;CDCl$_3$) 2.0 (6H, m), 2.9 (4H, m), 3.5 (2H, s), 5.9 (1H, d), and 7.3 (10H, m); m/z (LRMS) 350 (MH$^+$).

PREPARATION 10

3-Benzoyl-5-{4-(1-benzylpiperidinyl)}-1,2,4-oxadiazole

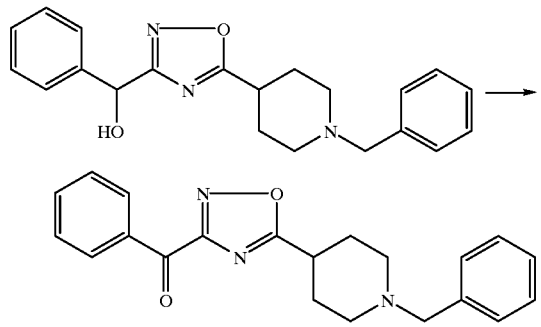

Manganese dioxide (206 g, 2.37 moles) was added portionwise to a mechanically stirred solution of 3-(α-hydroxybenzyl)-5-{4-(1-benzylpiperidinyl)}-1,2,4-oxadiazole (45.0 g, 0.19 moles) in dry THF (300 cm$^3$) at room temperature over a period of 2 hours. The resulting mixture was then stirred at room temperature for 45 minutes, filtered through an "Arbocel"™ pad, and concentrated under reduced pressure to give a tacky solid. This residue was redissolved in a minimum quantity of hot diisopropyl ether and the resulting solution was filtered then cooled in an ice-water bath to give the title compound as a beige crystalline solid (26 g, 75 mmoles, 58%). This material was identical in all respects to that prepared according to Preparation 5.

PREPARATION 11

3-(1,1-Diphenyl-1-hydroxymethyl)-5-(4-piperidinyl)-1,2,4-oxadiazole

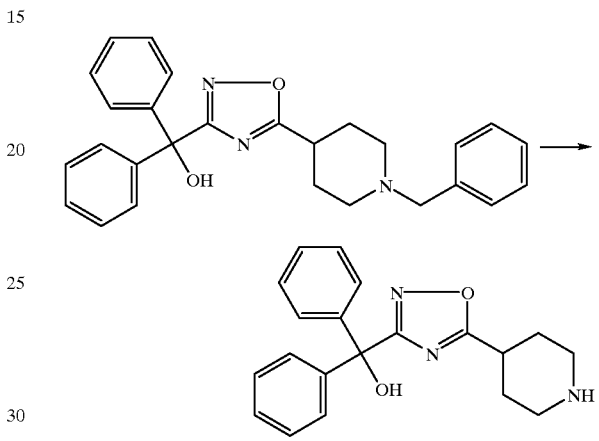

α-Chloroethylchloroformate (0.27 cm$^3$, 2.5 mmoles) was added dropwise to a stirred solution of 3-(1,1-diphenyl-1-hydroxymethyl)-5-{4-(1-benzylpiperidinyl)}-1,2,4-oxadiazole (1.00 g, 2.30 mmoles) in dry dichloromethane (10 cm$^3$) at 0° C. under nitrogen. The resulting solution was stirred at 0° C. for 40 minutes then concentrated under reduced pressure. The resulting residue was dissolved in methanol (20 cm$^3$) and heated at reflux for 40 minutes. The flask contents were then cooled, concentrated under reduced pressure and partitioned between dichloromethane (100 cm$^3$) and saturated aqueous sodium bicarbonate (50 cm$^3$). The organic fraction was dried over anhydrous sodium sulphate then concentrated under reduced pressure. Flash chromatography (25 g kieselgel 60 silica) eluting with 5 to 15% methanol in dichloromethane gave the title compound as a white foam (0.68 g, 2.0 mmoles, 80%), Rf 0.05 (90:10 CH$_2$Cl$_2$:MeOH), δ$_H$ (300 MHz;CDCl$_3$) 1.9 (2H, m), 2.2 (2H, m), 2.8 (2H, t), 3.1 (1H, m), 3.3 (2H, m), 4.2 (1H, b), and 7.4 (10H, m); m/z (LRMS) 336 (MH$^+$).

PREPARATION 12

3-(1-Cyclobutyl-1-phenyl-1-hydroxymethyl)-5-(4-piperidinyl)-1,2,4-oxadiazole

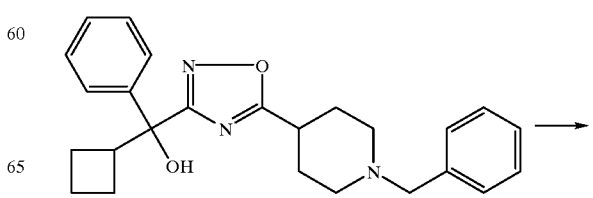

17
-continued

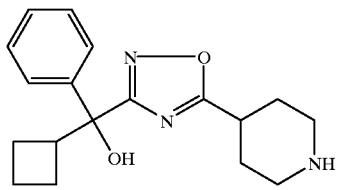

α-Chloroethylchloroformate (3.30 g, 23.0 mmoles) was added dropwise to a stirred solution of 3-(1-cyclobutyl-1-phenyl-1-hydroxymethyl)-5-{4-(1-benzylpiperidinyl)}-1,2,4-oxadiazole (8.52 g, 21.0 mmoles) in dry toluene (100 cm$^3$). The resulting mixture was then heated at reflux under nitrogen for 90 minutes. The flask contents were then allowed to cool and the reaction mixture concentrated under reduced pressure. The resulting residue was dissolved in methanol (50 cm$^3$) and heated at reflux for 40 minutes. The flask contents were then cooled, concentrated under reduced pressure and partitioned between dichloromethane (100 cm$^3$) and saturated aqueous sodium bicarbonate (50 cm$^3$). The organic fraction was dried over anhydrous sodium sulphate then concentrated under reduced pressure. Flash chromatography (25 g "Kieselgel 60" silica) eluting with 5 to 15% methanol in dichloromethane gave the title compound as a white foam (1.63 g, 5.2 mmoles, 23%), $\delta_H$ (300 MHz:CDCl$_3$) 1.7 (6H, m), 2.0 (4H, m), 2.7 (4H, m), 3.1 (1H, m), 3.2 (2H, m), 3.3 (1H, m), 7.3 (3H, m), and 7.5 (2H, d); m/z (LRMS) 315 (MH$^+$).

EXAMPLE 1

3-(1,1-Diphenyl-1-hydroxymethyl)-5-{4-(1-benzylpiperidinyl)}-1,2,4-oxadiazole

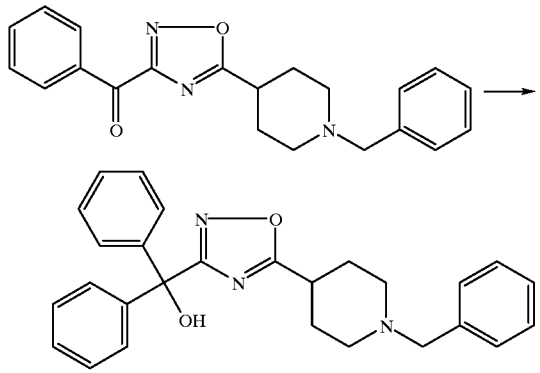

Phenyl lithium (5.0 cm$^3$; 1.8M in cyclohexane, 9.0 mmoles) was added dropwise to a stirred solution of 3-benzoyl-5-{4-(1-benzylpiperidinyl)}-1,2,4-oxadiazole (3.0 g, 8.6 mmoles) in dry tetrahydrofuran (40 cm$^3$) at −78° C. under a nitrogen atmosphere. The resulting solution was allowed to warm to room temperature over a period of two hours and was then partitioned between ethyl acetate (3×50 cm$^3$) and brine (20 cm$^3$). The combined organic fractions were then dried over anhydrous sodium sulphate and concentrated under reduced pressure. Flash chromatography (30 g "Kieselgel 60" silica) eluting with 35% ethyl acetate in hexane gave the title compound (2.9 g, 6.8 mmoles, 76%) Rf 0.8 (ethyl acetate), (Found C, 75.45;H, 6.4; N, 9.8. C$_{27}$H$_{27}$N$_3$O$_2$.¼H$_2$O requires C, 75.4; H, 6.45; N, 9.8 %); $\delta_H$ (300 MHz;CDCl$_3$) 2.0 (6H, m), 2.9 (2H, m), 3.5 (2H, s), 3.7 (1H, s), and 7.3 (15H, m); m/z (LRMS) 426 (MH$^+$).

18
EXAMPLE 2

3-(1-nButyl-1-phenyl-1-hydroxymethyl)-5-{4-(1-benzylpiperidinyl)}-1,2,4-oxadiazole

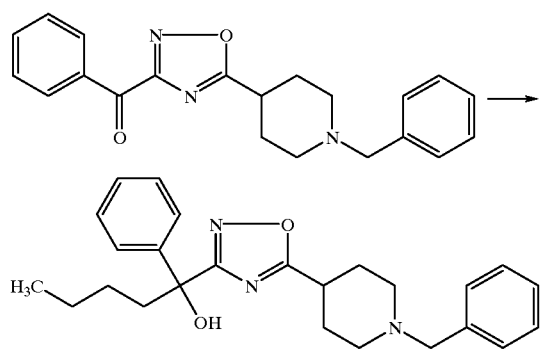

The title compound was prepared by a similar method to that described in Example 1 substituting butyl lithium (2.5 M in hexane, 1.1 mole equivalents) in place of phenyl lithium to give the title compound, (Found C, 73.5; H, 7.8; N, 10.0. C$_{25}$H$_{31}$N$_3$O$_2$ requires C, 74.0; H, 7.7; N, 10.4%); $\delta_H$ (300 MHz;CDCl$_3$) 0.8 (3H, m), 1.3 (4H, m), 2.1 (8H, m), 2.9 (3H, m), 3.2 (1H, s), 3.5 (2H, m), 7.3 (8H, m), and 7.5 (2H, d); m/z (LRMS) 406 (MH$^+$).

EXAMPLE 3

3-{1-(2-Thienyl)-1-phenyl-1-hydroxymethyl}-5-{4-(1-benzylpiperidinyl)}-1,2,4-oxadiazole

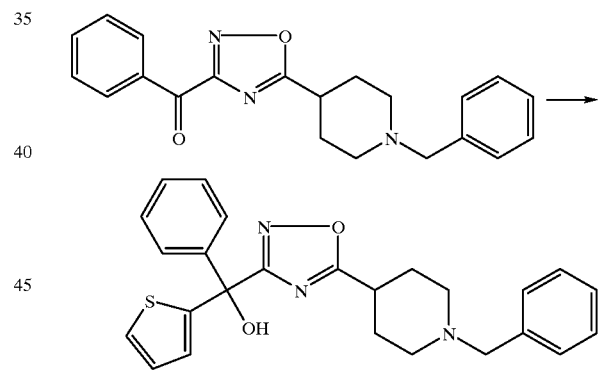

n-Butyl lithium (1.3 cm$^3$; 2.5M in hexane, 3.25 mmoles) was added dropwise to a stirred solution of thiophene (0.3 cm$^3$, 3.0 mmoles) in dry tetrahydrofuran (30 cm$^3$) under nitrogen at −78° C. and the resulting solution stirred at −78° C. for ten minutes to produce 2-thienyllithium. A solution of 3-benzoyl-5-{4-(1-benzylpiperidinyl)}-1,2,4-oxadiazole (1.0 g, 2.9 mmoles) in dry tetrahydrofuran (10 cm$^3$) was then added in one portion and the resulting mixture stirred at −78° C. for one hour. The cooling bath was then removed and the flask contents allowed to warm to room temperature over a period of one hour. The reaction mixture was then partitioned between ethyl acetate (3×50 cm$^3$) and brine (20 cm$^3$). The combined organic fractions were then dried over anhydrous sodium sulphate and concentrated under reduced pressure. Flash chromatography (30 g "Kieselgel 60" silica) eluting with 40% ethyl acetate in hexane then gave the title compound (0.83 g, 1.9 mmoles, 66%) (Found C. 68.6; H, 5.9; N, 9.5. $C_{25}H_{25}N_3O_2S.¼H_2O$ requires C, 68.9; H, 5.9; N, 9.6%); $\delta_H$ (300 MHz;CDCl$_3$) 2.1 (6H, m), 2.9 (3H, m), 3.5 (2H, s), 3.95 (1H, s), 6.9 (2H, m), 7.3 (9H, m), and 7.5 (2H, m); m/z (LRMS) 432 (MH$^+$).

EXAMPLES 4–9

The compounds of the following tabulated examples of the general formula shown below were prepared by reaction of 3-benzoyl-5-{4-(1-benzylpiperidinyl)}-1,2,4-oxadiazole with the appropriate organolithium agent using a similar method to that described in Example 3.

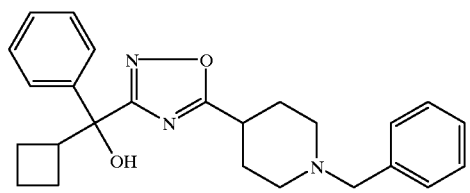

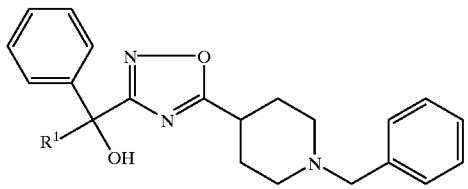

| Example | Organo lithium precursor | $R^1$ | LRMS | Analysis/$\delta_H$ (300 MHz; CDCl$_3$) |
|---|---|---|---|---|
| 4 | 2-bromopyridine | 2-pyridyl | 427 (MH$^+$) | Found C, 72.2; H, 6.2; N, 12.9. $C_{26}H_{26}N_4O_2.¼H_2O$ requires C, 72.5; H, 6.2; N, 13.0% $\delta_H$ (300 MHz; DCl$_3$) 2.0 (6H, m), 2.9 (3H, m), 3.5 (2H, s), 6.65 (1H, s), 7.3 (8H, m), 7.45 (3H, m), 7.7 (1H, t), and 8.6 (1H, d). |
| 5 | 4-bromopyridine | 4-pyridyl | 427 (MH$^+$) | Found C, 73.3; H, 6.1; N, 13.2. $C_{26}H_{26}N_4O_2$ requires C, 73.2; H, 6.1; N, 13.1% $\delta_H$ (300 MHz; CDCl$_3$) 2.0 (6H, m), 2.9 (3H, m), 3.5 (2H, s), 4.0 (1H, s), 7.3 (12H, m), and 8.5 (2H, d). |
| 6 | thiazole | 2-thiazolyl | 433 (MH$^+$) | Found C, 66.1; H, 5.5; N, 12.8. $C_{24}H_{24}N_4O_2S.¼H_2O$ requires C, 66.0; H, 5.65; N, 12.8% $\delta_H$ (300 MHz; CDCl$_3$) 2.0 (6H, m), 2.9 (3H, m), 3.5 (2H, s), 4.8 (1H, s), 7.3 (9H, m), 7.6 (2H, d), and 7.8 (1H, d). |
| 7 | benzothiazole | 2-benzothiazolyl | 484 (MH$^+$) | Found C, 69.9; H, 5.8; N, 11.1. $C_{28}H_{26}N_4O_2S$ requires C, 69.7; H, 5.4; N, 11.6% $\delta_H$ (300 MHz; CDCl$_3$) 2.0 (6H, m), 2.9 (3H, m), 3.5 (2H, s), 5.0 (1H, s), 7.3 (10H, m), 7.7 (2H, d), 7.85 (1H, d), and 8.05 (1H, d). |
| 8 | propargyl alcohol | HOCH$_2$C≡C— | 404 (MH$^+$) | Found C, 69.1; H, 6.2; N, 9.7. $C_{24}H_{25}N_3O_3.¾H_2O$ requires C, 69.1; H, 6.4; N, 10.1% $\delta_H$ (300 MHz; CDCl$_3$) 2.0 (6H, m), 2.9 (3H, m), 3.5 (2H, s), 4.4 (2H, s), 7.3 (8H, m), and 7.7 (2H, d). |
| 9 | 5-hexyne-1-ol | HO(CH$_2$)$_4$C≡C— | 446 (MH$^+$) | Found C, 72.1; H, 7.0; N, 9.4. $C_{27}H_{31}N_3O_3.¼H_2O$ requires C, 72.1; H, 7.05; N, 9.3% $\delta_H$ (300 MHz; CDCl$_3$) 1.7 (6H, m), 2.0 (7H, m), 2.4 (2H, t), 2.9 (3H, m), 3.5 (2H, s), 3.7 (2H, t), 7.3 (8H, m), and 7.7 (2H, d). |

EXAMPLE 10

3-(1-Cyclobutyl-1-phenyl-1-hydroxymethyl)-5-{4-(1-benzylpiperidinyl)}-1,2,4-oxadiazole

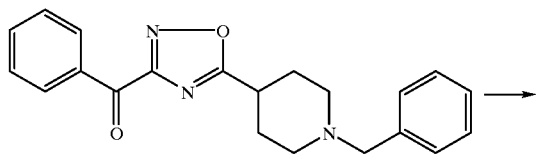

Cyclobutylbromide (21.7 cm$^3$, 0.23 moles) was added dropwise to a suspension of magnesium turnings (5.7 g, 0.23 moles) in dry diethyl ether (50 cm$^3$) at such a rate so as to maintain reflux. The resulting mixture was then stirred at room temperature for 30 minutes before being added dropwise to a stirred solution of 3-benzoyl-5-{4-(1-benzylpiperidinyl)}-1,2,4-oxadiazole (40.0 g, 0.115 moles) in diethyl ether (400 cm$^3$) and tetrahydrofuran (100 cm$^3$) at −10° C. under a nitrogen atmosphere. The resulting mixture was then allowed to warm to room temperature over a period of 2 hours. The flask contents were then cooled and saturated aqueous ammonium chloride (30 cm$^3$) added cautiously. Deionised water (500 cm$^3$) was then added and the mixture extracted with ethyl acetate (2×200 cm$^3$). The combined organic fractions were then dried over anhydrous sodium sulphate and concentrated under reduced pressure. Flash chromatography (500 g "Kieselgel 60" silica) eluting with 40–70% ethyl acetate in pentane then gave the title compound (31.5 g, 0.78 moles, 68%) (Found C, 73.0; H, 7.4; N, 10.1. $C_{25}H_{29}N_3O_2 \cdot \frac{1}{4}H_2O$ requires C, 73.5; H, 7.3; N, 10.3%); $\delta_H$ (300 MHz;CDCl$_3$) 1.9 (12H, m), 2.9 (3H, m), 3.2 (1H, s), 3.3 (1H, m), 3.5 (2H, s), 7.3 (8H, m), and 7.5 (2H, d); m/z (LRMS) 403 (MH$^+$). HPLC ("Chiralpak AD"™ column, 2.5×25 cm) eluting with 20% isopropanol, 0.06% trifluoroacetic acid, 0.03% diethylamine in hexane at 7 cm$^3$/minute then gave (−)-3-( 1-cyclobutyl-1-phenyl-1-hydroxymethyl)-5-{4-(1-benzylpiperidinyl)}-1,2,4-oxadiazole, $[\alpha]_D^{20}$ −48°, c 0.1, dichloromethane; and (+)-3-(1-cyclobutyl-1-phenyl-1-hydroxymethyl)-5-{4-(1-benzylpiperidinyl)}-1,2,4-oxadiazole, $[\alpha]_D$+51°, c 0.1 dichloromethane; (Found C, 74.3: H, 7.2: N, 10.4. $C_{25}H_{29}N_3O_2$ requires C, 74.4; H 7.2; N, 10.4%).

EXAMPLES 11–15

The compounds of the following tabulated examples of the general formula shown below were prepared by reaction of 3-benzoyl-5-{4-(1-benzylpiperidinyl)}-1,2,4-oxadiazole with the appropriate Grignard reagent using a similar method to that described in Example 10.

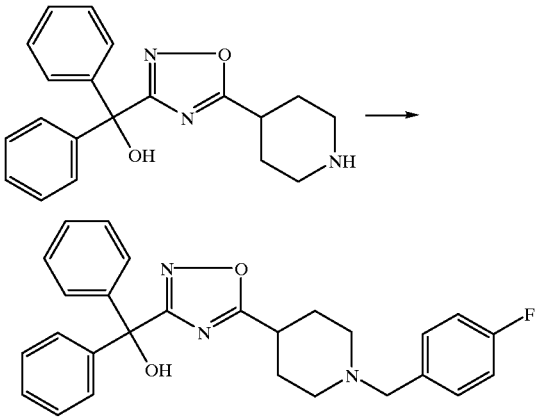

| Example | R$^1$ | LRMS | Analysis/ $\delta_H$ (300 MHz; CDCl$_3$) |
|---|---|---|---|
| 11 | cyclopentyl | 418 (MH$^+$) | Found C, 74.9; H, 7.7; N, 10.0. $C_{26}H_{31}N_3O_2$ requires C, 74.8; H, 7.5; N, 10.1% $\delta_H$ (300 MHz; CDCl$_3$) 1.4 (2H, m), 1.6 (6H, m), 2.05 (6H, m), 2.9 (4H, m), 3.2 (1H, s), 3.5 (2H, s), 7.3 (8H, m), and 7.6 (2H, d). |
| 12 | cyclohexyl | 432 (MH$^+$) | Found C, 74.3; H, 7.5; N, 9.55. $C_{27}H_{33}N_3O_2 \cdot \frac{1}{4}H_2O$ requires C, 74.4; H, 7.7; N, 9.6% $\delta_H$ (300 MHz; CDCl$_3$) 1.05 (3H, m), 1.15 (3H, m), 1.5 (3H, m), 1.7 (2H, m), 2.1 (6H, m), 2.9 (3H, m), 3.2 (1H, s), 3.5 (2H, s), 7.3 (8H, m), and 7.6 (2H, d). |
| 13 | 2-naphthyl | 475 (MH$^+$) | Found C, 77.7; H, 5.9; N, 8.8. $C_{31}H_{24}N_3O_2$ requires C, 78.3; H, 6.2; N, 8.8% $\delta_H$ (300 MHz; CDCl$_3$) 2.0 (6H, m), 2.9 (3H, m), 3.5 (2H, s), 3.9 (1H, s), 7.3 (8H, m), 7.5 (5H, m), and 7.9 (4H, m). |
| 14 | pentafluoroethyl | 468 (MH$^+$) | Found C, 59.1; H, 4.7; N, 9.0. $C_{23}H_{22}N_3O_2F_5$ requires C, 59.1; H, 4.7; N, 8.9% $\delta_H$ (300 MHz; CDCl$_3$) 2.0 (6H, m), 2.9 (3H, m), 3.5 (2H, s), 4.4 (1H, s), 7.3 (5H, m), 7.4 (3H, m), and 7.9 (2H, m). |

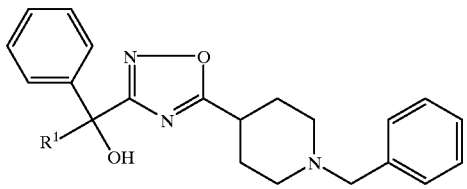

| Example | R$^1$ | LRMS | Analysis/ $\delta_H$ (300 MHz; CDCl$_3$) |
|---|---|---|---|
| 15 | ethynyl | 374 (MH$^+$) | Found C, 73.2; H, 6.5; N, 10.9. $C_{23}H_{23}N_3O_2 \cdot 1/20H_2O$ requires C, 73.3; H, 6.2; N, 11.1% $\delta_H$ (300 MHz; CDCl$_3$) 2.0 (6H, m), 2.9 (4H, m), 3.5 (2H, s), 3.9 (1H, b), 7.3 (8H, m), and 7.8 (2H, m). |

EXAMPLE 16

3-(1,1-Diphenyl-1-hydroxymethyl)-5-[4-{4-fluorophenylmethyl)piperidinyl}]-1,2,4-oxadiazole Solid sodium bicarbonate (0.20 g) was added to a stirred solution of 3-(1,1-diphenyl-1-hydroxymethyl)-5-(4-piperidinyl)-1,2,4-oxadiazole (0.20 g, 0.6 mmoles) and 4-fluoro-phenylmethyl chloride (0.075 cm$^3$, 0.6 mmoles) in dry dimethylformamide (1 cm$^3$). The resulting mixture was stirred under nitrogen at room temperature for 24 hours then partitioned between ethyl acetate (3×20 cm$^3$) and saturated aqueous sodium carbonate (20 cm$^3$). The combined organic fractions were then dried over anhydrous sodium sulphate and concentrated under reduced pressure. Flash chromatography (40 g "Kieselgel 60" silica) eluting with 30–50% ethyl acetate in hexane then gave the title compound (0.07 g, 0.16 mmoles, 26%) (Found C, 72.6; H, 5.95; N, 9.4. $C_{27}H_{26}N_3O_2F$ requires C, 73.1; H, 5.9; N, 9.5%); $\delta_H$ (300 MHz;CDCl$_3$) 2.1 (6H, m), 2.9 (3H, m), 3.5 (2H, s), 3.75 (1H, s), 6.95 (2H, d), and 7.4 (12H, m); m/z (LRMS) 444 (MH$^+$).

EXAMPLES 17 AND 18

The compounds of the following tabulated examples of the general formula shown below were prepared by reaction of 3-(1,1-diphenyl-l-hydroxymethyl)-5-(4-piperidinyl)-1,2, 4-oxadiazole with the appropriate alkyl halide using a similar method to that described in Example 16.

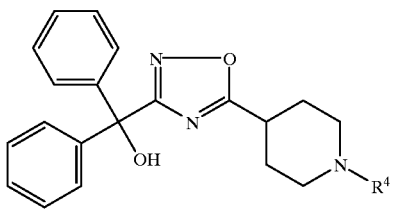

| Example | Alkyl halide | R⁴ | LRMS | Analysis/$\delta_H$ (300 MHz; CDCl$_3$) |
|---|---|---|---|---|
| 17 | 3,4-dichlorobenzyl chloride | (3,4-dichlorobenzyl group) | 494 (MH⁺) 496 (MH⁺) 498 (M⁺) | Found C, 65.5; H, 4.9; N, 8.6. $C_{27}H_{25}N_3O_2Cl_2$ requires C, 65.6; H, 5.1; N, 8.7% $\delta_H$ (300 MHz; CDCl$_3$) 2.1 (6H, m), 2.9 (3H, m), 3.5 (2H, s), 3.75 (1H, s), 7.1 (1H, d), and 7.4 (12H, m). |
| 18 | 5-(2-bromoethyl)-2,3-dihydrobenzofuran | (2,3-dihydrobenzofuranylethyl group) | 482 (MH⁺) | Found C, 74.9; H, 6.5; N, 8.6. $C_{30}H_{31}N_3O_3$ requires C, 74.8; H, 6.6; N, 8.7% $\delta_H$ (300 MHz; CDCl$_3$) 2.1 (6H, m), 2.5 (2H, m), 2.7 (2H, m), 3.0 (3H, m), 3.2 (2H, t), 3.9 (1H, s), 4.5 (2H, t), 6.7 (1H, d), 6.9 (1H, d), 7.0 (1H, s), and 7.4 (10H, m). |

EXAMPLE 19

3-(1-Cyclobutyl-1-phenyl-1-hydroxymethyl)-5-[4-{1-(4-methoxybenzyl)piperidinyl}]-1,2,4-oxadiazole

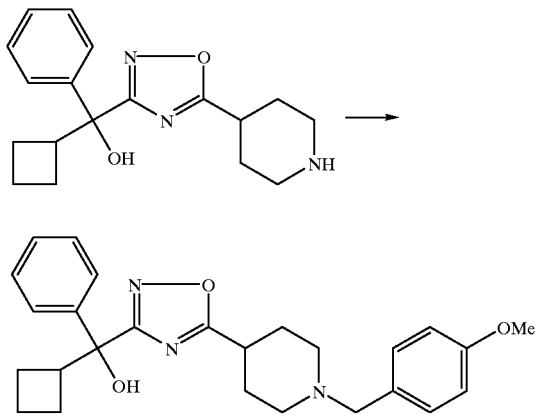

Acetic acid (0.04 g, 0.6 mmoles) was added to a stirred solution of 3-(1-cyclobutyl-1-phenyl-1-hydroxymethyl)-5-(4-piperidinyl)-1,2,4-oxadiazole (0.16 g, 0.5 mmoles) in dry tetrahydrofuran (15 cm³) at ambient temperature under nitrogen. 4-Methoxybenzaldehyde (0.082 g, 0.6 mmoles) and sodium triacetoxyborohydride (0.212 g, 1.0 mmoles) were then added and the resulting mixture stirred at ambient temperature under nitrogen for 6 hours. The flask contents were then partitioned between dichloromethane (100 cm³) and saturated aqueous sodium bicarbonate. The organic fraction was collected, dried over anhydrous sodium sulphate, and concentrated under reduced pressure to give a brown oil. Flash chromatography ("Kieselgel 60" silica) eluting with 30–50% ethyl acetate in hexane then gave the title compound (0.125 g, 0.28 mmoles, 56%) (Found C, 71.1; H, 7.25; N, 8.6. $C_{26}H_{31}N_3O_3 \cdot \frac{1}{3}H_2O$ requires C, 71.7; H, 7.2; N, 9.6%); $\delta_H$ (300 MHz;CDCl$_3$) 1.6–2.2 (12H, m), 3.2 (1H, s), 3.3 (1H, t), 3.4 (2H, s), 3.8 (3H, s), 6.95 (3H, m), 7.3 (4H, m), and 7.5 (2H, m); m/z (LRMS) 434 (MH⁺).

EXAMPLES 20 TO 25

The compounds of the following tabulated examples of the general formula shown below were prepared by reaction of 3-(1-cyclobutyl-1-phenyl-1-hydroxymethyl)-5-(4-piperidinyl)-1,2,4-oxadiazole with the appropriate aldehyde using a similar method to that described in Example 19.

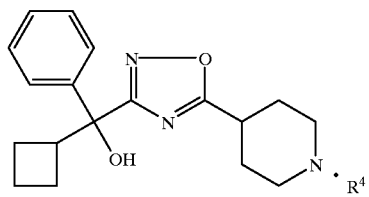

| Example | Aldehyde | R⁴ | LRMS | Analysis/$\delta_H$ (300 MHz; CDCl₃) |
|---|---|---|---|---|
| 20 | 4-hydroxybenzaldehyde | (4-hydroxyphenyl)ethyl | 420 (MH⁺) | Found C, 70.1; H, 6.9; N, 9.8. $C_{25}H_{29}N_3O_3 \cdot \frac{1}{2}H_2O$ requires C, 70.1; H, 7.1; N, 9.7% $\delta_H$ (300 MHz; CDCl₃) 1.8–2.1 (12H, m), 2.9 (3H, m), 3.1 (1H, s), 3.3 (1H, t), 3.4 (2H, s), 6.7 (2H, d), 7.1 (2H, d), 7.2 (3H, m), and 7.5 (2H, d). |
| 21 | cyclohexanecarboxaldehyde | cyclohexylethyl | 409 (MH⁺) | Found C, 71.3; H, 8.6; N, 9.8. $C_{25}H_{35}N_3O_2 \cdot 3/20 CH_2Cl_2$ requires C, 71.5; H, 8.4; N, 9.95% $\delta_H$ (300 MHz; CDCl₃) 0.8 (2H, m), 1.1 (3H, m), 1.4–2.1 (20H, m), 2.9 (3H, m), 3.1 (1H, s), 3.3 (1H, t), 7.1 (3H, m), and 7.5 (2H, d). |
| 22 | thiophene-2-carboxaldehyde | 2-thienylethyl | 410 (MH⁺) | Found C, 67.3; H, 6.7; N, 10.2. $C_{23}H_{27}N_3O_2S$ requires C, 67.5; H, 6.6; N, 10.3% $\delta_H$ (300 MHz; CDCl₃) 1.8–2.1 (12H, m), 2.9 (3H, m), 3.1 (1H, s), 3.3 (1H, t), 3.8 (2H, s), 6.9 (2H, m), 7.2 (4H, m), and 7.5 (2H, d). |
| 23 | phenylacetaldehyde | phenylpropyl | 418 (MH⁺) | Found C, 74.9; H, 7.5; N, 9.9. $C_{26}H_{31}N_3O_2$ requires C, 74.8; H, 7.4; N, 10.1% $\delta_H$ (300 MHz; CDCl₃) 1.8–2.1 (12H, m), 2.6 (2H, m), 2.8 (2H, m), 2.9 (3H, m), 3.1 (1H, s), 3.3 (1H, t), 7.2 (3H, m), 7.3 (5H, m), and 7.5 (2H, d). |
| 24 | 3,4-dichlorobenzaldehyde | 3,4-dichlorophenylethyl | 472 (MH⁺) | Found C, 60.6; H, 5.4; N, 7.2. $C_{25}H_{27}N_3O_2Cl_2$ requires C, 60.3; H, 5.5; N, 8.3% $\delta_H$ (300 MHz; CDCl₃) 1.8–2.1 (12H, m), 2.9 (3H, m), 3.1 (1H, s), 3.3 (1H, t), 3.4 (2H, s), 7.0–7.6 (8H, m). |
| 25 | 2,3-dihydrobenzo[b]furan-5-carboxaldehyde | 2,3-dihydrobenzofuran-5-ylethyl | 446 (MH⁺) | Found C, 72.2; H, 7.0; N, 9.0 $C_{27}H_{31}N_3O_3 \cdot \frac{1}{4}H_2O$ requires C, 72.1, H, 7.1, N, 9.4% $\delta_H$ (300 MHz; CDCl₃) 1.8–2.1 (10H, m), 2.9 (2H, m), 3.1 (2H, m), 3.3 (1H, m), 3.4 (2H, s), 4.5 (2H, t), 6.7 (1H, d), 7.0 (1H, d), 7.2 (1H, s), 7.2 (1H, s) 7.3 (3H, m) and 7.5 (2H, d). |

EXAMPLE 26

3-(1-Cyclobutyl-1-phenyl-1-hydroxymethyl)-5-[4-{1-(2-phenoxyethyl)piperidinyl}]-1,2,4-oxadiazole

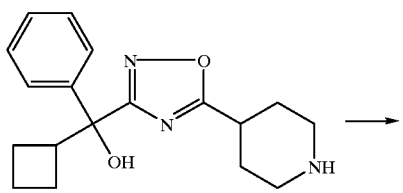

→

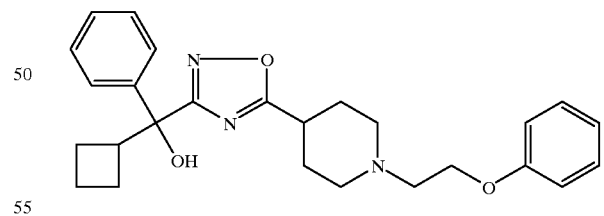

2-Phenoxybromoethane (0.10 g, 0.5 mmoles) was added to a solution of 3-(1-cyclobutyl-1-phenyl-1-hydroxymethyl)-5-(4-piperidinyl)-1,2,4-oxadiazole (0.16 g, 0.5 mmoles) in dry tetrahydrofuran (15 cm³) at ambient temperature under nitrogen. Ethyldiisopropylamine (0.13 g, 1.0 mmoles) was then added and the resulting solution stirred at ambient temperature for 7 days. The flask contents were then partitioned between ethyl acetate (3×30 cm³) and saturated aqueous sodium bicarbonate solution (10 cm³). The combined organic extracts were then dried and concentrated under reduced pressure. Flash chromatography ("Kieselgel 60" silica) eluting with 3% methanol in dichloromethane then gave the title compound (0.022 g, 0.05 mmoles, 10%) $^8$H (300 MHz;CDCl$_3$) 1.6–2.2 (10H, m), 2.3 (2H, t), 2.8 (2H, t), 2.9 (1H, m), 3.0 (2H, m), 3.2 (1H, s), 3.3 (1H, q), 4.1 (2H, t), 6.9 (3H, m), 7.3 (5H, m), and 7.5 (2H, m); m/z (LRMS) 434 (MH$^+$).

EXAMPLE 27

3-(1-Cyclobutyl-1-phenyl-1-hydroxymethyl)-5-[4-{1-(α-methylbenzyl)piperidinyl}]-1,2,4-oxadiazole

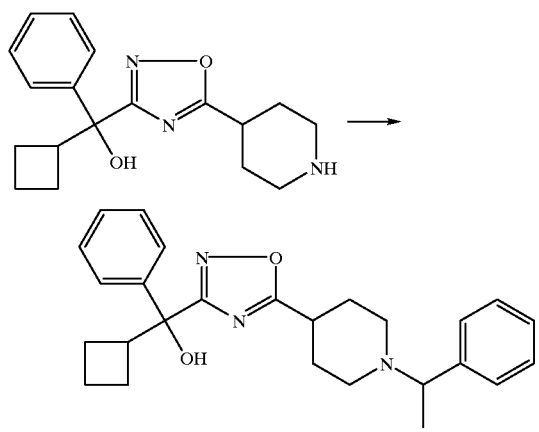

The above compound was prepared by reaction of 3-(1-cyclobutyl-1-phenyl-1-hydroxymethyl)-5-(4-piperidinyl)-1,2,4-oxadiazole with α-methylbenzyl bromide using a method similar to that described for Example 26.

(Found C, 73.8; H, 7.4; N, 9.6. C$_{26}$H$_{31}$N$_3$O$_2$.⅓H$_2$O requires C, 73.8; H, 7.5; N, 9.9 %); δ$_H$ (300 MHz;CDCl$_3$) 1.3 (3H, s), 1.6–2.2 (12H, m), 2.8 (2H, m), 3.0 (1H, m), 3.2 (1H, s), 3.3 (1H, t), 3.5 (1H, m), 7.2 (8H, m), and 7.5 (2H, m); m/z (LRMS) 419 (MH$^+$).

We claim:
1. A compound of the formula

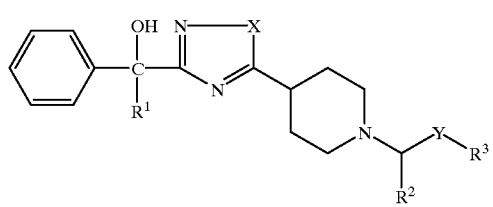

(I)

wherein R$^1$ is C$_1$–C$_6$ alkyl, halo-(C$_1$–C$_6$ alkyl), C$_3$–C$_7$ cycloalkyl, C$_2$–C$_6$ alkynyl, hydroxy-(C$_2$–C$_6$ alkynyl), (C$_1$–C$_4$ alkoxy)-(C$_2$–C$_6$ alkynyl), aryl, aryl-(C$_1$–C$_4$ alkyl), heteroaryl or heteroaryl-(C$_1$–C$_4$ alkyl);

R$^2$ is H or C$_1$–C$_4$ alkyl;

R$^3$ is aryl, heteroaryl, 2,3-dihydrobenzofuranyl or C$_4$–C$_7$ cycloalkyl;

X is O or S;

and Y is a direct link, —CH$_2$—, —(CH$_2$)$_2$— or —CH$_2$O—;

or a pharmaceutically acceptable salt thereof.

2. A compound as claimed in claim 1 wherein the aryl group is phenyl or naphthyl both optionally substituted by up to 3 substituents each independently selected from C$_1$–C$_4$ alkyl, C$_1$–C$_4$ alkoxy, hydroxy, halo and trifluoromethyl.

3. A compound as claimed in claim 2 wherein the aryl group is selected from phenyl optionally substituted by 1 or 2 substituents each independently selected from C$_1$–C$_4$ alkyl, C$_1$–C$_4$ alkoxy, hydroxy, halo and trifluoromethyl; and naphthyl.

4. A compound as claimed in claim 3 wherein the aryl group is phenyl, fluorophenyl, dichlorophenyl, hydroxyphenyl, methoxyphenyl or naphthyl.

5. A compound as claimed in claim 1 wherein the heteroaryl group is thienyl, pyridyl, thiazolyl, benzothiazolyl, thiadiazolyl, pyrazolyl or pyrimidinyl, all optionally substituted by 1 or 2 substituents each independently selected from C$_1$–C$_4$ alkyl, C$_1$–C$_4$ alkoxy, hydroxy and halo.

6. A compound as claimed in claim 5 wherein the heteroaryl group is thienyl, pyridyl, thiazolyl or benzothiazolyl.

7. A compound as claimed in claim 1 wherein R$^1$ is C$_1$–C$_6$ alkyl; pentafluoroethyl; C$_4$–C$_6$ cycloalkyl; ethynyl; —C≡C—CH$_2$OH; —C≡C—(CH$_2$)$_4$—OH;

a phenyl group optionally substituted by 1 or 2 substituents each independently selected from halo, C$_1$–C$_4$ alkyl, C$_1$–C$_4$ alkoxy and hydroxy; naphthyl; or a heterocyclic group selected from thienyl, pyridyl, thiazolyl and benzothiazolyl, all optionally substituted by halo, C$_1$–C$_4$ alkyl, C$_1$–C$_4$ alkoxy or hydroxy.

8. A compound as claimed in claim 1 wherein R$^2$ is H or CH$_3$.

9. A compound as claimed in claim 1 wherein R$^3$ is phenyl optionally substituted by 1 or 2 substituents each independently selected from halo, C$_1$–C$_4$ alkyl, C$_1$–C$_4$ alkoxy and hydroxy; 2,3-dihydrobenzofuranyl; C$_4$–C$_7$ cycloalkyl or thienyl.

10. A compound as claimed in claim 1 wherein X is O.

11. A compound as claimed in claim 1 wherein Y is a direct link, —CH$_2$— or —CH$_2$O—.

12. 3-(1-Cyclobutyl-1-phenyl-1-hydroxymethyl)-5-[4-(1-benzylpiperidinyl)]-1,2,4-oxadiazole; or (+)-3-(1-cyclobutyl-1-phenyl-1-hydroxymethyl)-5-[4-(1-benzylpiperidinyl)]-1,2,4-oxadiazole.

13. A pharmaceutical composition comprising a compound of the formula (I) or pharmaceutically acceptable salt thereof as claimed in claim 1 and a pharmaceutically acceptable diluent or carrier.

14. A compound of the formula (II):

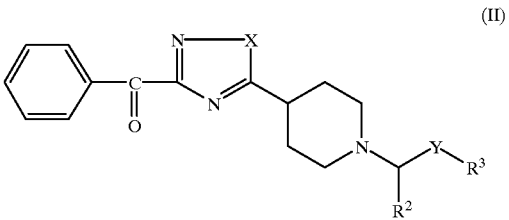

(II)

where X, Y, R$^2$ and R$^3$ are as defined in claim 1.

15. A process for preparing a compound of the formula (I) as claimed in claim 1 or a pharmaceutically acceptable salt thereof, which comprises reacting a compound of the formula (II) as claimed in claim 14 without a Grignard, organolithium or organocerium reagent of the formula:

$R^1MgHal$, $R^1Li$ or $R^1CeCl_2$ where Hal is Cl or Br and $R^1$ is as defined in claim 1, in an organic solvent; said process being followed by, optionally, conversion of the product of the formula (I) into a pharmaceutically acceptable salt.

16. A process according to claim 15, wherein a reagent of the formula $R^1MgBr$ or $R^1Li$ is used, $R^1$ being as defined in claim 15.

17. A process for preparing a compound of the formula (I) as claimed in claim 1, or a pharmaceutically acceptable salt thereof, which comprises the reaction of a compound of the formula (III) or base salt thereof:

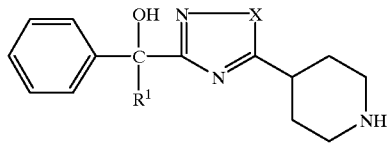

(III)

wherein $R^1$ and X are as defined in claim 1, with either (a) a compound of the formula (IV):

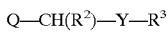

(IV)

wherein Q is a leaving group and $R^2$, $R^3$ and Y are as defined in claim 1; or (b) an aldehyde or ketone of the formula

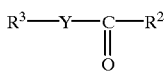

(V)

wherein $R^2$, $R^3$ and Y are as defined in claim 1, in the presence of a reducing agent and in an organic solvent; said process being followed by, optionally, conversion of the product of the formula (I) into a pharmaceutically acceptable salt.

18. A process as claimed in claim 17, wherein the leaving group is tosyloxy, mesyloxy, trifluoromethanesulfonyloxy, Cl or Br, and wherein the reducing agent is sodium triacetoxyborohydride or sodium cyanoborohydride.

19. A process as claimed in claim 17 wherein when the free base of compound (III) is used in (a), and the reaction is carried out in the presence of an acid acceptor.

20. A process according to claim 19 wherein the acid acceptor is sodium bicarbonate or ethyidiisopropylamine.

21. A process claim according to claim 15 for preparing the compound 3-(1-cyclobutyl-1-phenyl-1-hydroxymethyl)-5-[4-(1-benzylpiperidinyl)]-1,2,4-oxadiazole, characterised by reacting cyclobutylmagnesium bromide with 3-benzoyl-5-[4-(1-benzylpiperidinyl)]-1,2,4-oxadiazole, followed by, if desired, separating said compound into its (+) and (−) enantiomers.

22. A process according to claim 21, characterised in that separation is carried out by HPLC.

23. A method of treating irritable bowel syndrome, diverticular disease, urinary incontinence, oesophageal achalasia or chronic obstructive airways disease in a human patient in need of such treatment, which comprises administering to said patient a muscarinic receptor antagonistic effective amount of a compound or pharmaceutically acceptable salt thereof as claimed in claim 1.

\* \* \* \* \*